United States Patent
Palmer

(10) Patent No.: US 10,293,136 B2
(45) Date of Patent: May 21, 2019

(54) EFFICIENTLY PACKAGED READY TO USE INTERMITTENT URINARY CATHETER

(71) Applicant: CURE MEDICAL, LLC, Newport Beach, CA (US)

(72) Inventor: Timothy Palmer, Stillwater, MN (US)

(73) Assignee: Cure Medical, LLC, Newport Beach, CA (US)

(*) Notice: Subject to any disclaimer, the term of this patent is extended or adjusted under 35 U.S.C. 154(b) by 373 days.

(21) Appl. No.: 15/130,337

(22) Filed: Apr. 15, 2016

(65) Prior Publication Data

US 2017/0296776 A1    Oct. 19, 2017

(51) Int. Cl.
| | | |
|---|---|---|
| *A61M 25/00* | (2006.01) | |
| *B65D 75/30* | (2006.01) | |
| *B65D 81/22* | (2006.01) | |

(52) U.S. Cl.
CPC ...... *A61M 25/002* (2013.01); *A61M 25/0017* (2013.01); *B65D 75/30* (2013.01); *B65D 81/22* (2013.01)

(58) Field of Classification Search
CPC ............ A61M 25/0017; A61M 25/002; A61M 25/0111; A61M 25/0113; B65D 75/30; B65D 81/22; B65D 81/24
USPC ........ 206/210, 363, 364, 438; 604/172, 265, 604/544
See application file for complete search history.

(56) References Cited

U.S. PATENT DOCUMENTS

| | | | |
|---|---|---|---|
| 3,345,988 | A | 10/1967 | Vitello |
| 3,750,875 | A | 8/1973 | Juster |
| 3,854,483 | A | 12/1974 | Powers |
| 3,934,721 | A | 1/1976 | Juster et al. |
| 3,967,728 | A | 7/1976 | Gordon et al. |
| 4,230,115 | A | 10/1980 | Walz, Jr. et al. |
| 5,147,341 | A | 9/1992 | Starke et al. |
| 5,226,530 | A | 7/1993 | Golden |
| 5,895,374 | A | 4/1999 | Rodsten |
| 6,004,305 | A | 12/1999 | Hursman et al. |
| 6,053,905 | A | 4/2000 | Daignault, Jr. et al. |
| 6,065,597 | A | 5/2000 | Pettersson et al. |
| 6,090,075 | A | 7/2000 | House |
| 6,391,010 | B1 | 5/2002 | Wilcox |
| 6,578,709 | B1 | 6/2003 | Kavanagh et al. |
| 6,602,244 | B2 | 8/2003 | Kavanagh et al. |
| 6,634,498 | B2 | 10/2003 | Kayerod et al. |
| 6,638,269 | B2 | 10/2003 | Wilcox |
| 6,848,574 | B1 | 2/2005 | Israelsson et al. |
| 6,849,070 | B1 | 2/2005 | Hansen et al. |
| 6,887,230 | B2 | 5/2005 | Kubalak et al. |

(Continued)

FOREIGN PATENT DOCUMENTS

| | | |
|---|---|---|
| EP | 677299 A1 | 10/1995 |
| EP | 1498151 A2 | 1/2005 |

(Continued)

*Primary Examiner* — Bryon P Gehman
(74) *Attorney, Agent, or Firm* — Sherrill Law Offices, PLLC

(57) ABSTRACT

An efficiently packaged ready to use intermittent urinary catheter. The catheter is retained within a retention chamber having a profile that mimics the profile of the catheter by sealing the upper and a lower films together along a peripheral seal line. The retention chamber includes an enlarged compartment intermediate axial ends of the catheter in which lubricant is stored.

22 Claims, 4 Drawing Sheets

(56) References Cited

U.S. PATENT DOCUMENTS

| | | |
|---|---|---|
| 7,001,370 B2 | 2/2006 | Kubalak et al. |
| 7,094,220 B2 | 8/2006 | Tanghoj et al. |
| 7,150,739 B2 | 12/2006 | O'Niel |
| 7,160,590 B2 | 1/2007 | Vanhamel et al. |
| 7,311,698 B2 | 12/2007 | Tanghoj et al. |
| 7,328,794 B2 | 2/2008 | Lubs et al. |
| 7,334,679 B2 | 2/2008 | Givens et al. |
| 7,458,964 B2 | 12/2008 | Mosler et al. |
| 7,476,223 B2 | 1/2009 | McBride |
| 7,517,343 B2 | 4/2009 | Tanghoj et al. |
| 7,601,142 B2 | 10/2009 | House |
| 7,601,158 B2 | 10/2009 | House |
| 7,662,146 B2 | 2/2010 | House |
| 7,682,353 B2 | 4/2010 | Tanghoj et al. |
| 7,766,163 B2 | 8/2010 | Tanghoej |
| 7,770,726 B2 | 8/2010 | Murray et al. |
| 7,823,722 B2 | 11/2010 | Bezou et al. |
| 7,886,907 B2 | 2/2011 | Murray et al. |
| 7,918,831 B2 | 4/2011 | House |
| 7,922,712 B2 | 4/2011 | Tanghoj et al. |
| 8,011,505 B2 | 9/2011 | Murray et al. |
| 8,051,981 B2 | 11/2011 | Murray et al. |
| 8,052,673 B2 | 11/2011 | Nestenborg |
| 8,066,693 B2 | 11/2011 | Tanghoj et al. |
| 8,127,922 B2 | 3/2012 | Nordhilm et al. |
| 8,177,774 B2 | 5/2012 | House |
| 8,201,689 B2 | 6/2012 | Kaem |
| 8,205,745 B2 | 6/2012 | Murray et al. |
| 8,230,993 B2 | 7/2012 | Tanghoej |
| 8,317,775 B2 | 11/2012 | House |
| 8,356,457 B2 | 1/2013 | Murray et al. |
| 8,414,562 B2 | 4/2013 | House |
| 8,459,455 B2 | 6/2013 | Frojd |
| 8,523,843 B2 | 9/2013 | Kavanagh et al. |
| 8,567,602 B2 | 10/2013 | Niederberger et al. |
| 8,579,115 B2 | 11/2013 | Murphy et al. |
| 8,668,683 B2 | 3/2014 | Golden |
| 8,720,685 B2 | 5/2014 | Murray et al. |
| 8,740,863 B2 * | 6/2014 | Nestenborg .......... A61M 25/002 604/171 |
| 9,033,149 B2 * | 5/2015 | Terry .................. A61M 25/002 206/364 |
| 9,314,585 B2 * | 4/2016 | Nestenborg .......... A61M 25/002 |
| 9,833,592 B1 * | 12/2017 | Palmer ................ A61M 25/002 |
| 9,872,970 B2 * | 1/2018 | Schonfeldt ........ A61M 25/0017 |
| 9,925,352 B2 * | 3/2018 | McBurney ........ A61M 25/0017 |
| 2005/0109648 A1 | 5/2005 | Kerzman et al. |
| 2006/0058777 A1 | 3/2006 | Nielsen |
| 2009/0000970 A1 | 1/2009 | Bordeau et al. |
| 2013/0144271 A1 | 6/2013 | Passadore et al. |
| 2013/0153446 A1 * | 6/2013 | Utas .................... A61M 25/002 206/210 |
| 2014/0257250 A1 * | 9/2014 | Palmer ................ A61M 25/002 604/544 |
| 2016/0220784 A1 * | 8/2016 | Palmer ............. A61M 25/0017 |

FOREIGN PATENT DOCUMENTS

| | | |
|---|---|---|
| EP | 909249 B1 | 4/2005 |
| GB | 1465544 | 2/1977 |
| WO | 9806642 | 2/1998 |
| WO | 2006121508 A2 | 11/2006 |
| WO | 2013158270 A1 | 10/2013 |

* cited by examiner

EFFICIENTLY PACKAGED READY TO USE INTERMITTENT URINARY CATHETER

BACKGROUND

Intermittent catheters are typically used by patients suffering from urinary incontinence or by individuals unable to enjoy voluntary urination. In our highly mobile culture, the ability to have the freedom to leave home for the day or longer is an important part of life. To accommodate this need single use catheters have been developed to allow patients to perform self catheterization. An individual requiring catheterization will typically utilize several catheters each and every day. This results in the usage of a large number of catheters over time, driving a demand for inexpensive catheters without sacrificing safety and comfort.

The high daily utilization rate for intermittent urinary catheters also results in the need for individuals requiring catheterization to transport several catheters with them whenever they leave the house for any extended period of time. Packaged catheters tend to be large and bulky, rendering it difficult to discretely transport a supply of catheters.

Accordingly, a need exists for an inexpensive and efficiently packaged intermittent urinary catheter, particularly one that is self-contained and ready for use immediately upon removal from the packaging.

SUMMARY OF THE INVENTION

The invention is an efficiently packaged, ready to use intermittent urinary catheter. The packaged catheter includes, and except for appropriate labeling and marking preferably only includes, (i) an intermittent urinary catheter, (ii) packaging formed from first and second layers of film, and (iii) a lubricant. The catheter has a longitudinal axial length, an insertion end, a funnel end and a top view profile, and is hermetically packaged between the first and second layers of film within a retention chamber formed from the films. The retention chamber has a top view profile conforming to the top view profile of the catheter and retains a supply of lubricant. In an alternative embodiment, the lubricant is predominately retained within an enlarged lubricant retaining compartment formed in the retention chamber intermediate the insertion and funnel ends of the catheter.

DETAILED DESCRIPTION OF A PREFERRED EMBODIMENT

Nomenclature
10 Packaged Intermittent Urinary Catheter
20 Catheter
$20_{Pf}$ Top View Profile of Catheter
$20x$ Axial Length of Catheter
21 Insertion End of Catheter
22 Fixture End or Funnel End of Catheter
30 Fixture or Funnel
40 Packaging
$40_{Py}$ Peripheral Edge of Packaging
41 First Layer of Packaging
42 Second Layer of Packaging
45 Margins of Packaging
$45w$ Width of Margins
49 Retention Chamber
$49_{Pf}$ Top View Profile of Retention Chamber
$49_{Py}$ Periphery of Retention Chamber
$49_{Lube}$ Lubricant Containing Compartment
$49_{Neck}$ Metering Neck Area of Retention Chamber
50 Lubricant
x Longitudinal or Axial Direction
y Lateral (Radial) Direction
z Transverse (Radial) Direction
Definitions As utilized herein, including the claims, the term "fixture" means and refers to the well known commercially available components commonly attached to the proximal non-insertion end of urinary catheters, including specifically but not exclusively funnels, luer locks, clamps, valves, etc.

As utilized herein, including the claims, the term "predominant" means at least 80%.

Description

Figure 1:
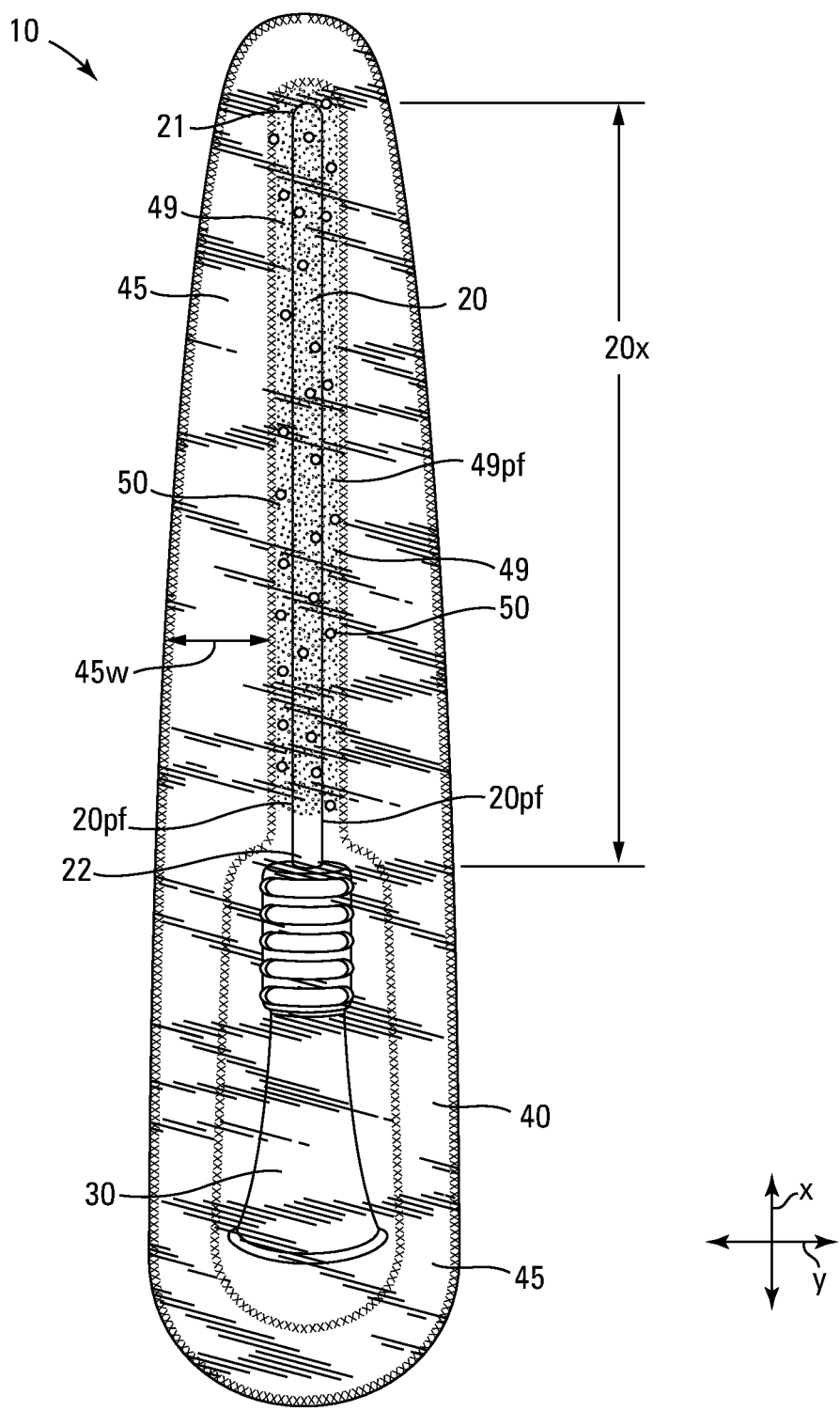
FIG. 1 is a top view of one embodiment of the invention.
Figure 2:
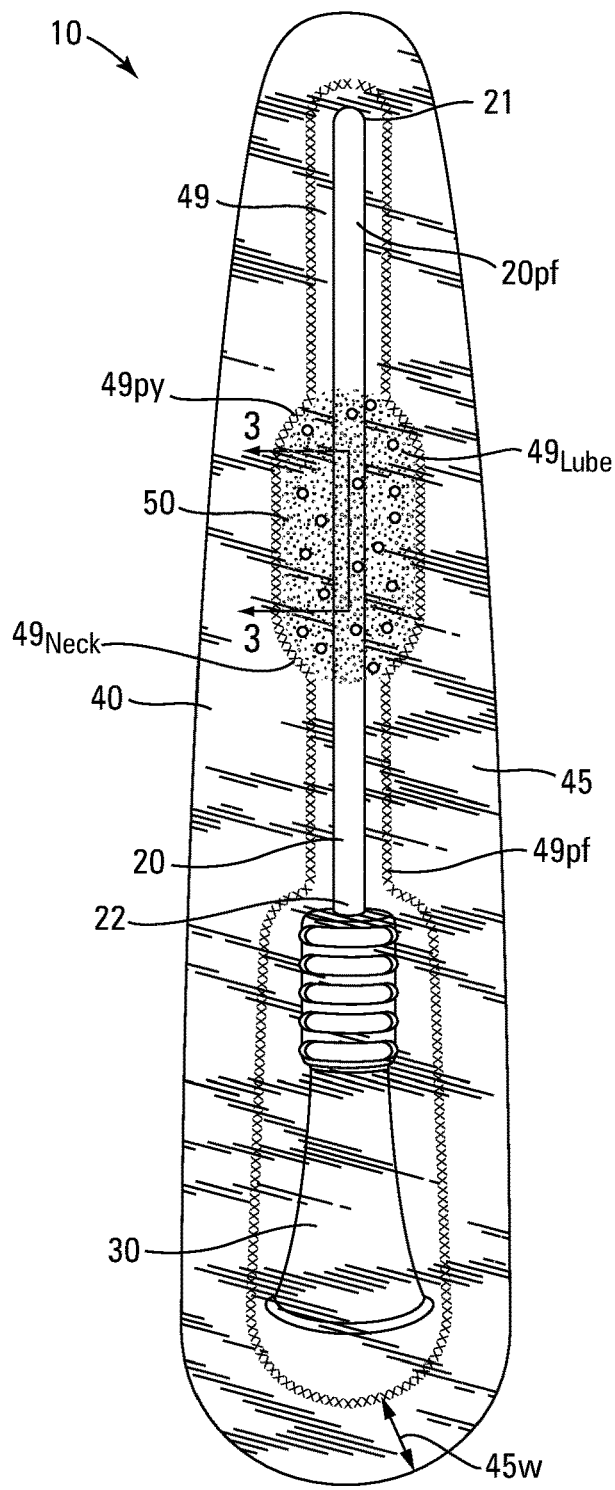
FIG. 2 is a top view of another embodiment of the invention
Figure 3:
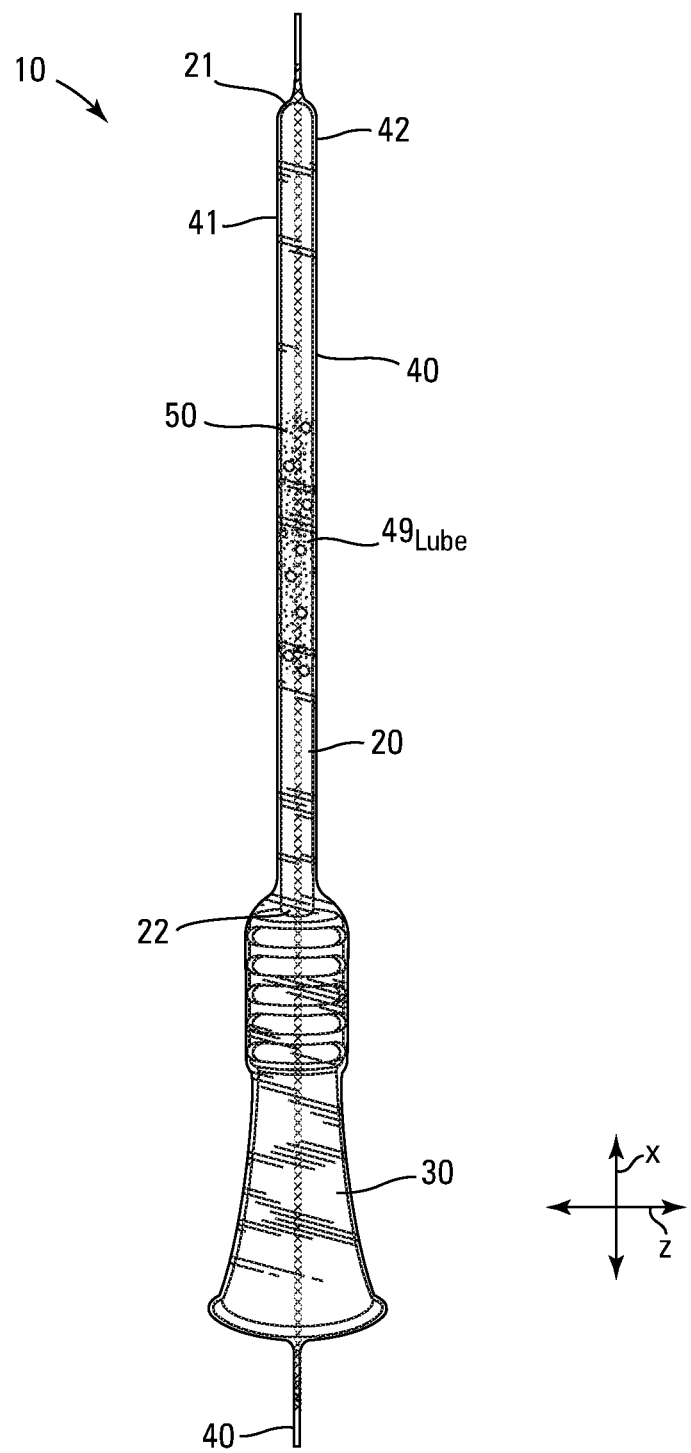
FIG. 3 is a side view of the invention depicted in FIG. 2.
Figure 4:
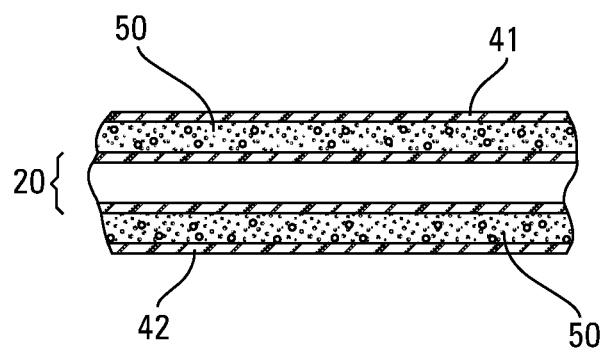
FIG. 4 is an enlarged cross-sectional side view of a portion of the invention depicted in FIGS. 2 and 3 taken along line 4-4.

The invention is an efficiently packaged, ready to use intermittent urinary catheter 10. Referring to FIGS. 1-3, the packaged catheter 10 includes, and in a preferred embodiment only includes, the functional components of, (i) an intermittent urinary catheter 20 equipped with a fixture 30 at one end, (ii) packaging 40 formed from first 41 and second 42 layers of film, and (iii) a lubricant 50.

The catheter 20 has an axial length $20x$ with an insertion end 21 and a fixture end 22. The catheter 20 defines a top view profile $20_{Pf}$. The packaging 40 may be used with substantially any commercially available catheter 20, but is particularly suited for use with shorter female urinary catheters.

The catheter 20 is hermetically packaged within a retention chamber 49 formed between first 41 and second 42 films sealed together, preferably by heat seal, within a peripheral margin 45 of the packaging 40. The films 41 and 42 may have originated from separate and independent rolls or sheets of film, or they may have been formed by simply folding a single length of film back upon itself. The packaging 40 formed by the first 41 and second 42 films defines an outer peripheral edge $40_{Py}$. The retention chamber 49 has a periphery $49_{Py}$ defining a top view profile $49_{Pf}$ that generally conforms to the top view profile $20_{Pf}$ of the catheter, except for an enlarged compartment $49_{Lube}$ intermediate the insertion 21 and funnel 22 ends of the catheter 20 in which lubricant 50 is stored for coating the catheter 20 when it is withdrawn from the packaging 40 for use. The enlarged compartment $49_{Lube}$ is preferably axially aligned with the balance of the retention chamber 49 such that the catheter 20 passes through the enlarged compartment $49_{Lube}$.

Referring to FIGS. 1 and 2, the margins 45 have a preferred width $45w$ of between 0.2 and 5 cm, most preferred between about 0.3 and 2 cm, around the entire periphery of the retention chamber 49.

The packaging layers 41 and 42 may be constructed from the same or different films, with the films selected from materials that are impervious to the lubricant 50, and suitable for hermetically sealing the catheter 20 within a retention chamber 49 formed from the films 41 and 42. Suitable materials include specifically but not exclusively, films of polyester, polyethylene, polypropylene, Surlyn®, Tyvek®, aluminum, Mylar®, etc.

Referring to FIGS. 1 and 2, the retention chamber 49 has a top view profile $49_{Pf}$ that tightly matches the top view profile $20_{Pf}$ of the catheter 20 along a predominant portion of the axial length $20x$ of the catheter 20 for purposes of maintaining lubricant 50 retained within the retention chamber 49 in close proximity to the catheter 20 so that the lubricant 50 will adhere to and coat the catheter 20 as the catheter 20 is withdrawn from the packaging 40. The profiles are preferably matched such that the axial cross-sectional area of the retention chamber 49 (i.e., the cross-sectional area of the retention chamber 49 in a plane extending in the lateral y and transverse z directions and perpendicular to the longitudinal x axis of the catheter 20) is between 1.2 and 1.8 times the corresponding axial cross-sectional area of the catheter 20 along at least 50%, preferably along at least 80% and preferably along at least 90% of the axial length $20x$ of the catheter 20.

Referring to FIG. 2, when the retention chamber 49 includes an expanded lubricant containing compartment $49_{Lube}$, the axial cross-sectional area of the lubricant containing compartment $49_{Lube}$ is between 2 and 4 times the largest axial cross-sectional area of the catheter 20 lying within the compartment 49Lube as packaged. The lubricant containing compartment $49_{Lube}$ necks down at the longitudinal x end of the compartment $49_{Lube}$ proximate the fixture end 22 of the catheter 20, preferably necking down at both longitudinal x ends, to an axial cross-sectional area that is between 1.2 and 1.8 times the largest axial cross-sectional area of the catheter 20 lying within the compartment $49_{Lube}$ as packaged. This necked down area $49_{Neck}$ formed from the packaging films 41 and 42, serves to meter the coating of lubricant 50 on the catheter 20 as the catheter 20 is withdrawn from the packaging 40 for use.

I claim:

1. A hermetically packaged intermittent urinary catheter, consisting essentially of: an intermittent urinary catheter having a longitudinal axial length with a first portion terminating at an insertion end and a second portion longitudinally opposed to the first portion terminating at a fixture end, and a top view profile, the catheter hermetically packaged between laminated first and second layers of film hermetically sealing the catheter within a lubricant containing retention chamber having a top view profile conforming to the top view profile of the catheter, wherein the lubricant is positioned and arranged within the retention chamber for lubricating contact with only the first portion of the packaged catheter.

2. The hermetically packaged intermittent urinary catheter of claim 1 wherein (i) the retention chamber has a longitudinal axial length, (ii) a portion of the longitudinal axial length of the retention chamber intermediate the insertion and fixture ends of the catheter has an expanded top view profile forming a lubricant containing compartment, and (iii) the lubricant retained within the retention chamber is predominantly retained within the lubricant containing compartment.

3. The hermetically packaged intermittent urinary catheter of claim 1 wherein the top view profile of the retention chamber is defined by a peripheral heat seal line.

4. The hermetically packaged intermittent urinary catheter of claim 3 wherein the first and second layers form packaging having a peripheral margin surrounding the retention chamber extending from the interior edge of the heat seal line to the outside periphery of the layers, and the peripheral margin is between 0.2 and 5 cm wide around the entire periphery of the retention chamber.

5. The hermetically packaged intermittent urinary catheter of claim 4 wherein the entire area of the peripheral margins is heat sealed.

6. The hermetically packaged intermittent urinary catheter of claim 3 wherein the first and second layers form packaging having a peripheral margin surrounding the retention chamber extending from the interior edge of the heat seal line to the outside periphery of the layers, and the peripheral margin is between 0.5 and 2 cm wide around the entire periphery of the retention chamber.

7. The hermetically packaged intermittent urinary catheter of claim 2 wherein the catheter extends axially through the lubricant containing compartment.

8. The hermetically packaged intermittent urinary catheter of claim 7 wherein the axial cross-sectional area of the lubricant containing compartment is between 2 and 4 times the largest axial cross-sectional area of that length of the catheter lying within the lubricant containing compartment as packaged.

9. The hermetically packaged intermittent urinary catheter of claim 7 wherein the lubricant containing compartment necks down to a narrower length of the retention chamber at one axial end of the lubricant containing compartment, thereby metering withdrawal of lubricant from the lubricant containing compartment as a coating upon the catheter during axial withdrawal of the catheter from the retention chamber.

10. The hermetically packaged intermittent urinary catheter of claim 9 wherein the axial cross-sectional area of the lubricant containing compartment is between 2 and 4 times the largest axial cross-sectional area of that length of the catheter lying within the lubricant containing compartment as packaged, and the axial cross-sectional area of the narrower length of the retention chamber is between 1.2 and 1.8 times the radially corresponding axial cross-sectional area of the catheter.

11. The hermetically packaged intermittent urinary catheter of claim 2 wherein the catheter and the retention chamber have radially corresponding axial cross-sectional areas along the axial length of the catheter, and the axial cross-sectional area of the retention chamber is between 1.2 and 1.8 times the radially corresponding axial cross-sectional area of the catheter along at least 50% of the axial length of the catheter.

12. The hermetically packaged intermittent urinary catheter of claim 1 wherein the catheter has an axial cross-sectional area in an alpha plane extending perpendicular to the longitudinal axis of the catheter, positioned proximate the fixture end of the catheter, the retention chamber has an axial cross-sectional area in the alpha plane, and the axial cross-sectional area of the retention chamber in the alpha plane is between 1.2 and 1.8 times the axial cross-sectional area of the catheter in the alpha plane.

13. The hermetically packaged intermittent urinary catheter of claim 1 wherein the catheter and the retention chamber have radially corresponding axial cross-sectional areas along the axial length of the catheter, and the axial cross-sectional area of the retention chamber is between 1.2 and 1.8 times the radially corresponding axial cross-sectional area of the catheter along at least 50% of the axial length of the catheter.

14. The hermetically packaged intermittent urinary catheter of claim 1 wherein the catheter and the retention chamber have radially corresponding axial cross-sectional areas along the axial length of the catheter, and the axial cross-sectional area of the retention chamber is between 1.2 and 1.8 times the radially corresponding axial cross-sectional area of the catheter along at least 80% of the axial length of the catheter.

15. The hermetically packaged intermittent urinary catheter of claim 1 wherein the catheter and the retention chamber have radially corresponding axial cross-sectional areas along the axial length of the catheter, and the axial cross-sectional area of the retention chamber is between 1.2 and 1.8 times the radially corresponding axial cross-sectional area of the catheter along 90% of the axial length of the catheter.

16. A hermetically packaged intermittent urinary catheter, consisting of: an intermittent urinary catheter having a longitudinal axial length with a first portion terminating at an insertion end and a second portion longitudinally opposed to the first portion terminating at a fixture end with or without an attached fixture, and a top view profile, the catheter hermetically packaged between laminated first and second layers of film hermetically sealing the catheter within a lubricant containing retention chamber having a top view profile conforming to the top view profile of the catheter, wherein the lubricant is positioned and arranged within the retention chamber for lubricating contact with only the first portion of the packaged catheter.

17. The hermetically packaged intermittent urinary catheter of claim 16 wherein the top view profile of the retention chamber is defined by heat sealed peripheral margins of the films.

18. The hermetically packaged intermittent urinary catheter of claim 16 wherein the first and second layers form packaging having a peripheral margin surrounding the retention chamber extending from the interior edge of a heat seal line to the outside periphery of the layers, and the peripheral margin is between 0.5 and 2 cm wide around the entire periphery of the retention chamber.

19. The hermetically packaged intermittent urinary catheter of claim 18 wherein the entire area of the peripheral margins is heat sealed.

20. A hermetically packaged intermittent urinary catheter, consisting of: an intermittent urinary catheter having a longitudinal axial length with a first portion terminating at an insertion end and a second portion longitudinally opposed to the first portion terminating at a fixture end with or without an attached fixture, and a top view profile, the catheter hermetically packaged between laminated first and second layers of film hermetically sealing the catheter within a retention chamber having a top view profile conforming to the top view profile of the catheter except for an expanded lubricant containing compartment of the retention chamber intermediate the insertion and funnel ends of the catheter.

21. The hermetically packaged intermittent urinary catheter of claim 20 wherein the axial cross-sectional area of the lubricant containing compartment is between 2 and 4 times the largest axial cross-sectional area of that length of the catheter lying within the lubricant containing compartment as packaged.

22. The hermetically packaged intermittent urinary catheter of claim 20 wherein the lubricant containing compartment necks down to a narrower length of the retention chamber at an axial end of the lubricant containing compartment proximate the fixture end of the catheter, thereby metering withdrawal of lubricant from the lubricant containing compartment as a coating upon the catheter during axial withdrawal of the catheter from the retention chamber.

* * * * *